(12) United States Patent
Arndt

(10) Patent No.: US 7,728,314 B2
(45) Date of Patent: Jun. 1, 2010

(54) INFRA-RED SOURCE AND GAS SENSOR

(75) Inventor: Michael Arndt, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 235 days.

(21) Appl. No.: 10/532,332

(22) PCT Filed: Dec. 9, 2003

(86) PCT No.: PCT/DE03/04040

§ 371 (c)(1), (2), (4) Date: Apr. 22, 2005

(87) PCT Pub. No.: WO2004/068120

PCT Pub. Date: Aug. 12, 2004

(65) Prior Publication Data

US 2006/0151723 A1 Jul. 13, 2006

(30) Foreign Application Priority Data

Jan. 22, 2003 (DE) ................ 103 02 165

(51) Int. Cl.
*G01J 3/10* (2006.01)
(52) U.S. Cl. .............. 250/504 R; 313/486; 422/3
(58) Field of Classification Search .......... 250/504 R
See application file for complete search history.

(56) References Cited

U.S. PATENT DOCUMENTS

| 3,211,961 | A | * | 10/1965 | Bayly et al. | 361/177 |
| 3,331,941 | A |   | 7/1967  | Edwards et al. | |
| 4,158,133 | A | * | 6/1979  | Spaeth et al. | 250/214 R |
| 4,500,810 | A | * | 2/1985  | Graff | 313/486 |
| 5,429,805 | A | * | 7/1995  | Uno et al. | 422/83 |
| 5,493,442 | A | * | 2/1996  | Buchholz et al. | 359/359 |
| 5,726,798 | A | * | 3/1998  | Bushman | 359/359 |

FOREIGN PATENT DOCUMENTS

| JP | 5 072130    | 3/1993 |
| JP | 6 108955    | 4/1994 |
| JP | 9 113446    | 5/1997 |
| JP | 2001 108617 | 4/2001 |
| WO | WO 00 04351 | 1/2000 |

OTHER PUBLICATIONS

Smith,S.D., "Design of Multilayer Filters by Considering Two Effective Interfaces",Jan. 1958, J. Opt. Soc. Amer., v. 48, No. 1, pp. 43-50.*

* cited by examiner

*Primary Examiner*—David A. Vanore
*Assistant Examiner*—Phillip A. Johnston
(74) *Attorney, Agent, or Firm*—Kenyon & Kenyon LLP

(57) ABSTRACT

An infrared source and a gas sensor, a first layer and a second layer effecting bandpass filter characteristics for an operating frequency range.

18 Claims, 3 Drawing Sheets

INFRA-RED SOURCE AND GAS SENSOR

BACKGROUND INFORMATION

Devices are known for the detection of radiation signals which may be used, for example, to determine the gas concentration, using infrared absorption. Interfering gases in a gas volume, such as in the passenger compartment of a motor vehicle, are, for example, $CO_2$, CO, $H_2O$ or even $CH_4$, the carbon dioxide $CO_2$ originating from especially the air breathed by people located in the gas volume and also from $CO_2$ air conditioning systems. Such interfering gases are detected by generally known gas detectors. Such detectors for the selection of gases, based on the principle of radiation absorption in the measured gas, are usually made up of a radiation source and one or more wavelength-specific radiation detectors. For sensors which measure the absorption in the medium infrared range, such as in the range of wavelengths of 3 μm to 25 μm, such as sensors for the detection of carbon dioxide $CO_2$, usually thermal radiators are used as the source. In this connection, there are infrared sources in the form of incandescent lamps or in the form of microstructured devices that function as thermal radiators. Wavelength-specific radiation detectors are made up of a filter unit which transmits the wavelength to be measured and a broad-band infrared detector. Interference filters are used in this connection, for example. Simple interference filters have the property of also transmitting harmonics of the desired wavelength. This may be rectified, first, by a more complicated and, thus, more cost-intensive construction of the interference filter, or also by putting a simple broadband filter before the actual detector. If such a broadband filter is used, this conditions a costly construction of the detector, since in that case two filters have to be mounted.

SUMMARY OF THE INVENTION

The infrared source and the gas sensor according to the present invention have the advantage that no additional assembly effort is necessary in the production of the sensor, and, all the same, a broadband filter is provided between the infrared source and the infrared detector. It is thus advantageously possible that the radiation emitted by the infrared source is emitted only in the range of the operating frequency range, and thus the dissipation of energy in other regions of the gas sensor will also be reduced. Thereby it is possible that the main heat development is only in the infrared source. The heat development may, in this context, be removed from the detector side. In addition, it is thereby possible according to the present invention, that only radiation in the narrow operating frequency range, about the wavelength of the interference filter, reaches in the direction of the detector at all.

It is especially advantageous that the first transmission characteristics with respect to the operating frequency range provides a higher transmission for shorter wavelengths, and that the second transmission characteristics with respect to the operating frequency range provides a higher transmission for greater (longer) wavelengths. Thereby it is possible in a simple manner to bring about bandpass filter characteristics for an operating frequency range. In addition, it is of advantage that, as the first layer, glass is provided and that, as the second layer, silicon or germanium is provided. In this context, it is possible to provide the bandpass characteristics according to the present invention using simple methods and materials, in the case of the glass layer, the material in the case of a usual infrared source already being available.

DETAILED DESCRIPTION

Figure 9:
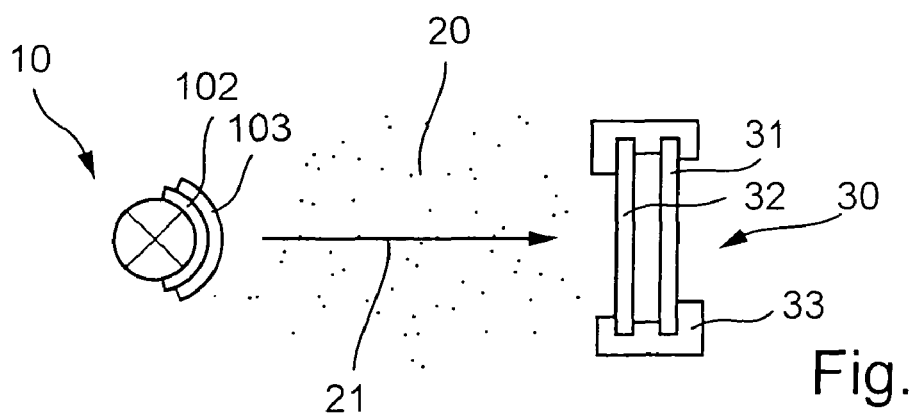
FIG. 9 shows the fundamental construction of the gas sensor according to the present invention.

FIG. 9 shows the fundamental construction of a gas sensor according to the present invention. Starting from an infrared source designated by reference numeral 10, which bears a first layer 102 and a second layer 103, an infrared radiation is emitted that is designated by reference numeral 21 and an arrow, in a direction towards a detector 30. In the region between infrared source 10 and detector 30, a gas is present that is provided with reference numeral 20. The gas includes gas proportions whose concentration is to be measured using the gas sensor. Carbon dioxide $CO_2$, for example, comes into consideration as such a gas proportion. Detector device 30 includes an infrared detector 31 and a filter 32, which are fixed relatively to each other by a holding device 33. Filter 32 according to the present invention only lets through a wavelength that corresponds to the absorption wavelength of the measured gas to be detected in gas 20, such as $CO_2$. From the degree of attenuation of infrared radiation 21, starting from the infrared source, for the measured wavelengths or detected wavelengths, the gas concentration of the gas to be measured, such as $CO_2$ in gas 20 may be derived. For this, it makes sense, according to the present invention, that, besides a device shown in FIG. 9 of a gas sensor, a reference device is provided at the same time, in which a filter is situated in front of a similar infrared detector, which lets through a greater wavelength range, so that hereby a reference measurement is carried out.

In the gas sensor shown in FIG. 9, filter 32 is provided, in particular, as an interference filter. For instance, filter 32 may be provided as a Fabry-Perot filter. Such filters have the property that, besides the desired pass frequency or the desired pass wavelength, additional pass frequencies or desired pass wavelengths occur. The desired pass frequency in this case corresponds to the absorption frequency of the substance in gas 20, whose concentration is to be measured. The additional pass frequencies or pass wavelengths of filter 32 are especially the harmonics of the desired pass wavelength. According to the present invention, it is prevented, using simple means, that undesired pass frequencies of filter 32 reach the region of infrared detector 31. To do this, according to the present invention, it is provided, in the case of considerable portions of infrared radiation 21 at these undesired pass frequencies, to hinder their further spreading in the direction of filter 32 or infrared detector 31, already shortly after their creation, i.e. at source 10. A device in which such a filtering out of undesired pass frequencies takes place immediately before or after filter 32, in this context is avoided according to the present invention, because this is connected with high costs and great expenditure with respect to the construction of detector 30. Therefore, according to the present invention, infrared source 10 is changed in such a way that only infrared radiation 21 is able to exit in a tight range about the desired pass frequency or pass wavelength of interference filter 32.

Figure 1:
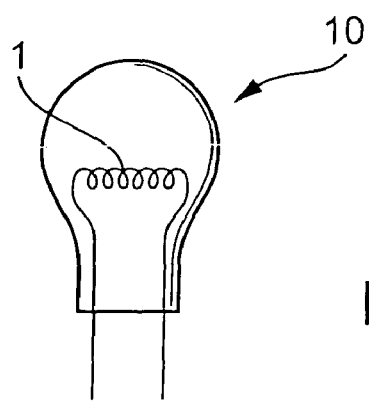
FIG. 1 shows a usual infrared source in the form of an incandescent lamp.

FIG. 1 shows a usual infrared source 10 for an infrared radiator in the form of an incandescent lamp. In this, a coiled filament that is heated to an appropriate temperature produces a radiation that also includes infrared proportions. According to the related art, the coiled filament is provided with an enclosing glass element.

Figure 2:
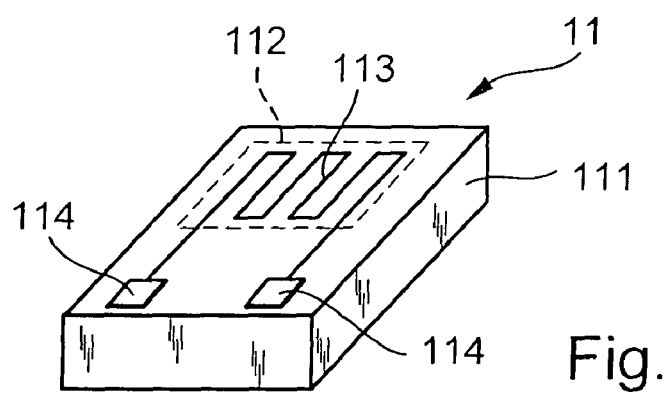
FIG. 2 shows a usual infrared source in the form of a micromechanical infrared radiator.

FIG. 2 shows a usual infrared source 11 in the form of a micromechanical infrared radiator. Micromechanical infrared source 11 includes a substrate 111, on which, especially, a diaphragm or a diaphragm region 112, and in diaphragm region 112 a heating structure 113 is provided. Heating structure 113 also designated as heating device 113 is (electrically) accessible or controllable using connecting areas marked with reference numerals 114, and not especially using connecting lines from outside micromechanical infrared source 11. In a manner similar to heating coil 1 in the usual infrared source according to FIG. 1, heating device 113 is heated up by an electric current flowing through it, and thereby generates the radiation, which also has infrared proportions.

Figure 3:
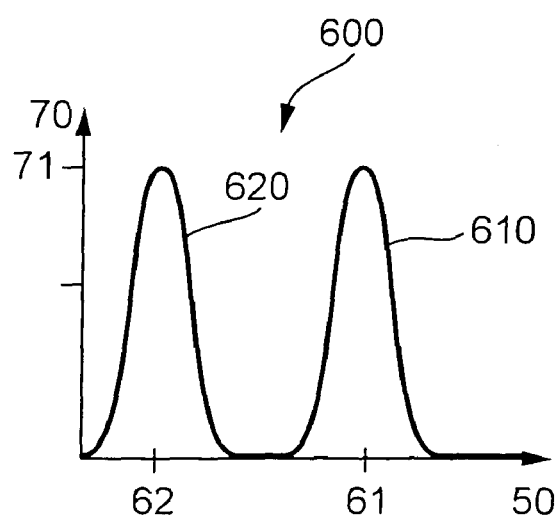
FIG. 3 shows the transmission curve of a customary interference filter.

FIG. 3 illustrates the transmission curve of a usual interference filter. On the abscissa denoted by reference numeral 50, the wavelength is shown, and on the ordinate marked by reference numeral 70, the degree of transmission is shown. A first degree of transmission of 100%, indicated by reference numeral 71, is reached only by particular wavelengths. Transmission curve 600 demonstrates maxima in the case of such particular wavelengths. Thus it breaks down into a number of transmission sub-curves centered about certain wavelengths, of which only two are shown in FIG. 3, namely, a first filter transmission sub-curve 610 and a second filter transmission sub-curve 620. First filter transmission sub-curve 610 is centered about the first transmission wavelength of the filter, which corresponds to the eleventh wavelength 61. Second filter transmission sub-curve 620 is centered about a twelfth wavelength, which is provided with reference numeral 62. Eleventh and twelfth wavelengths 61, 62 come about from twice the optical thickness of the material of the interference filter divided by an integer, the integer being able to assume the values 1, 2, etc.

Figure 4:
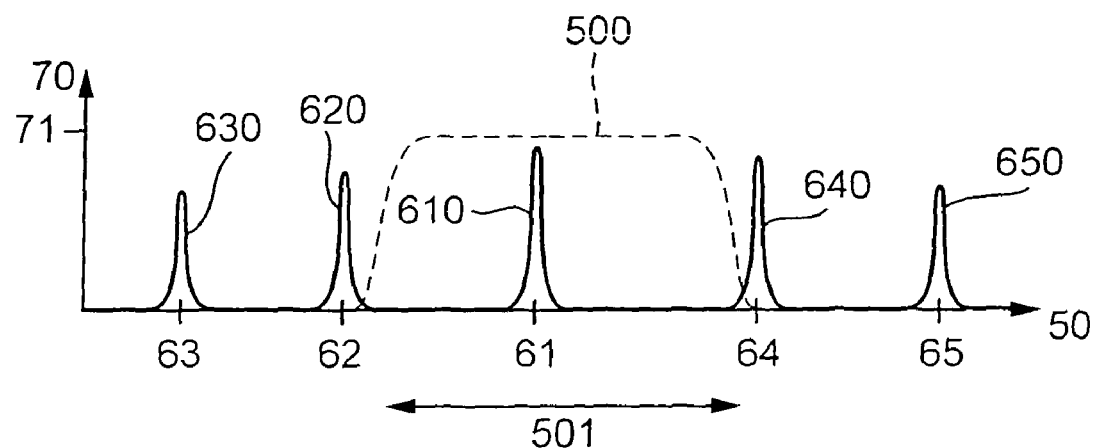
FIG. 4 shows the filter transmission curve and the transmission characteristics of the radiation emitted by an infrared source according to the present invention.

FIG. 4 shows the filter transmission curve and the transmission characteristics of the radiation emitted by an infrared source 10 according to the present invention. On the abscissa denoted by reference numeral 50, once again the wavelength is shown, and on the ordinate marked by reference numeral 70, the degree of transmission in % is shown. The characteristics of radiation radiated by a source according to the present invention is denoted by reference numeral 500 and a dashed line. This only assumes significant values in a range that includes only a maximum of the filter transmission curve. The whole filter transmission curve is shown in FIG. 4 in the light of several filter transmission sub-curves corresponding to eleventh wavelength 61, to twelfth wavelength 62, to a thirteenth wavelength 63, to a fourteenth wavelength 64 and to a fifteenth wavelength 65. The entire filter transmission curve 600, reference numeral 600 not being shown in FIG. 4, includes first filter transmission sub-curve 610 to eleventh wavelength 61, second filter transmission sub-curve 620 to twelfth wavelength 62, third filter transmission sub-curve 630 to thirteenth wavelength 63, a fourth filter transmission sub-curve 640 to fourteenth wavelength 64, and a fifteenth filter transmission sub-curve 650 to fifteenth wavelength 65. Once again, the maximum of the transmission of 100% is designated by the first degree of transmission 71. In FIG. 4, eleventh wavelength 61 is plotted in approximately the medium range of abscissa 50 shown, that is, the axis of the wavelengths. To the right and the left thereof, i.e. in the direction of the greater wavelengths and in the direction of the shorter wavelengths, the closest maxima of filter transmission curve 600 are at twelfth wavelength 62 and at fourteenth wavelength 64. About eleventh wavelength 61, characteristics 500 of the radiation radiated by infrared source 10 according to the present invention are shown, in the lower part of FIG. 4 the region of the operating frequencies or the operating wavelengths marked by a double arrow and reference numeral 501 agreeing approximately with the region of significant values of characteristics 500 of the radiation radiated by infrared source 10 according to the present invention.

Figure 5:
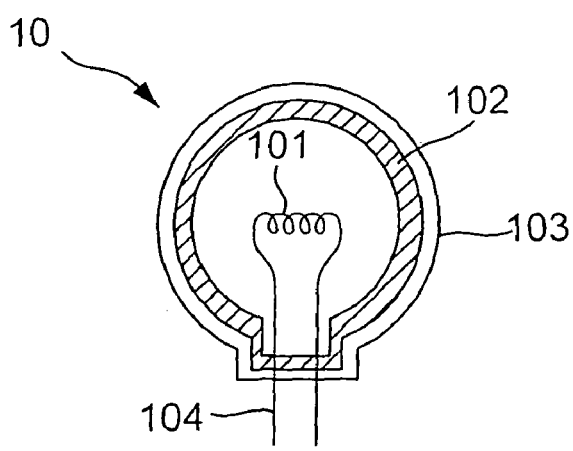
FIG. 5 shows an infrared source according to the present invention.

An infrared source 10 according to the present invention is shown in FIG. 5. In this connection, for example, infrared source 10 according to the present invention is provided as an incandescent lamp having a coiled filament 101 and connecting wires 104. Around coiled filament 101 there is a lamp glass element 102, made of glass, which acts as a first layer 102. An additional absorption layer 103 applied to this lamp glass element 102 is designated as the second layer. In this connection, in the first place, the absorption characteristics of the lamp glass 102, and in the second place the absorption characteristics of the additionally applied coating 103 of lamp glass 102 are used. The advantage of this construction lies in the utilization of lamp glass element 102 as a part of the absorption filter, to wit, as first layer 102 and additionally as carrier for an additional absorption filter layer 103, i.e. of second layer 103. For use in a $CO_2$ sensor which works, for example, based on an absorption measurement at a wavelength of 4.3 μm, typically a lamp glass is used which demonstrates a transmission up to a wavelength of ca 5 μm. These absorption characteristics have the effect that the longer-wave harmonics of interference filter 32 no longer count at detector 30, because they are absorbed by first layer 102. i.e. in this case, by lamp glass element 102. Consequently, the shorter wave components of the light radiated by filament 101 have to be filtered out in order to arrive at bandwidth-limited transmission characteristics 500 of the combination of the first and second layers 102, 103, as shown in FIG. 4. For this, semiconductor materials, for example, such as silicon or germanium are suitable, which are able to be vapor deposited as second layer 103 onto the surface of first layer 102, i.e. onto the surface of glass element 102 of the incandescent lamp. Besides semiconductor materials, however, metal layers or organic absorption layers may also be applied to the surface of first layer 102.

Figure 6:
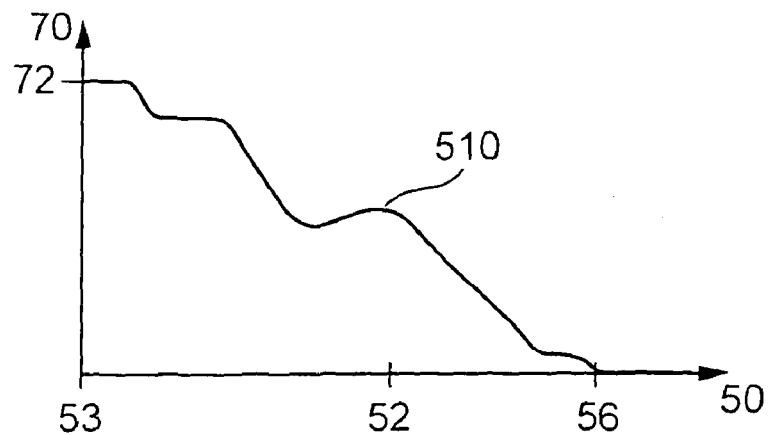
FIG. 6 shows the transmission characteristics of a first layer.

FIG. 6 shows the transmission characteristics 510 of first layer 102. In a diagram whose abscissa 50 represents a wavelength scale and whose ordinate 70 shows the degree of transmission of first layer 102, transmission characteristics 510 of first layer 102 are shown as the so-called first transmission characteristics 510. At a third wavelength 53, which is at about 2.5 μm, a second transmission rate 72 of about 90% comes about. Transmission 70 drops off towards greater wavelengths, at a second wavelength of about 4 μm a local maximum of the transmission characteristics of about 60% transmission coming about, and in the direction of greater wavelengths a relatively severe drop-off in transmission being observable, and at a sixth wavelength 56 of ca 5 μm transmission being close to 0. The transmission remains near 0% for greater wavelengths than sixth wavelength 56, and for shorter wavelengths than wavelength 53 it remains approximately at the level of second transmission rate 72 of ca 90%.

Figure 7:
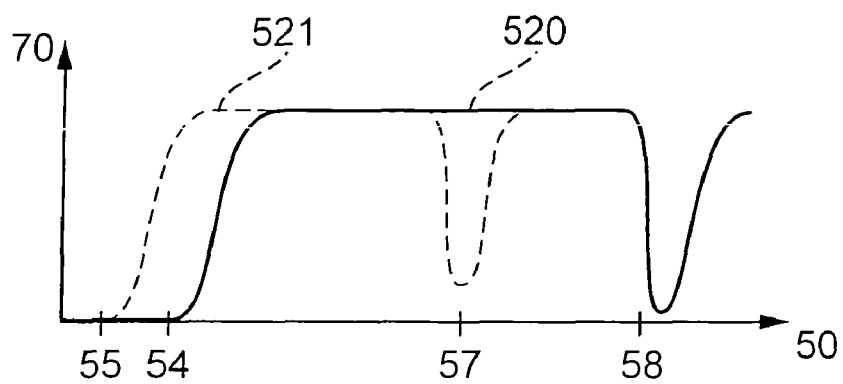
FIG. 7 shows the transmission characteristics of a second layer.

FIG. 7 shows transmission characteristics 520 and 521 of second layer 103. Once again, a diagram is selected whose abscissa 50 represents a wavelength scale, and whose ordinate 70 represents a scale of the transmission rate. Two transmission characteristics are shown in FIG. 7, both of them being designated as so-called second transmission characteristics. Second transmission characteristics marked by reference numeral 520 corresponds to transmission characteristics of a second layer 103 in the form of a germanium layer, and second transmission characteristics marked by reference numeral 521 shows the transmission characteristics for the case that second layer 103 is provided as a silicon layer. However, the shape of second transmission characteristics 520, 521 is similar in both cases: From a certain wavelength on, the transmission rate rises from about 0 to a maximum value of 90% or 100%, and remains essentially at this high transmission level up to a greater wavelength, at which a strong falling off in the transmission rate may be observed. For the second transmission characteristics (for germanium) designated by reference numeral 520, the transmission strongly increases beginning at a fourth wavelength of ca 1.7 μm, so as to drop off again at wavelengths beginning at an eighth wavelength 58 of over 20 μm. In the case of the second transmission characteristics (for silicon) designated by reference numeral 521, the transmission begins, already at a fifth wavelength 55 of clearly less than 1.7 μm, to clearly rise in order to remain on a high transmission level, until the transmission once more assumes lower values at a seventh wavelength 57 at ca 10 μm.

Figure 8:
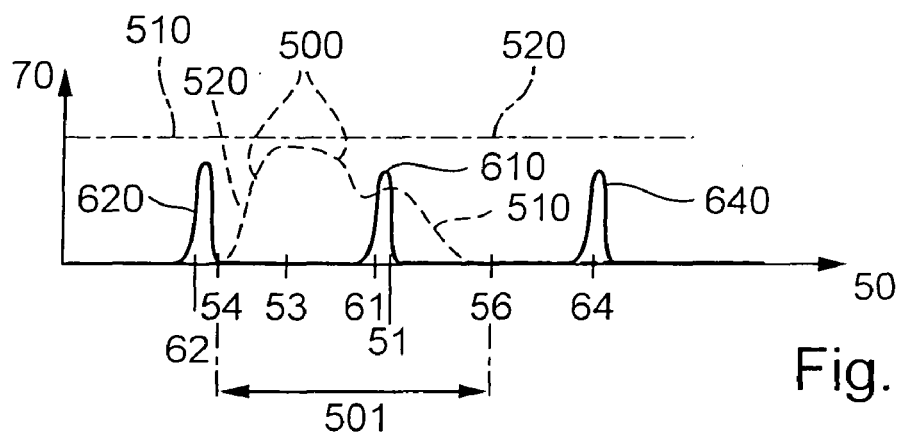
FIG. 8 shows the combination of the transmission characteristics with a filter transmission curve.

In FIG. 8, in an additional diagram, the combination is shown of the first and second transmission characteristics together with a filter transmission curve of the interference filter. In the diagram, once more, abscissa 50 forms a wavelength scale, and ordinate 70 forms a scale of the transmission rate. First transmission characteristics 510 are shown in FIG. 8 using a dash-dotted line, and it corresponds to the transmission characteristics for glass, shown in FIG. 6, below third wavelength 53, i.e. for wavelengths shorter than third wavelength 53, the transmission level being very high, between third wavelength 53 and sixth wavelength 56 a drop in the transmission to nearly 0 of first transmission characteristics 510 being shown. Second transmission characteristics 520 is shown in FIG. 8 by a dashed line and strongly rises above fourth wavelength 54, i.e. for greater wavelengths than the fourth wavelength, so as then to persevere above values of sixth wavelength 56 at this high transmission value. A superimposition of the two transmission characteristics yields the band filter characteristics according to the present invention that is designated in FIG. 8 by reference numeral 500, and which includes the two falling off or rising branches of first and second transmission characteristics 510, 520. Such bandpass filter characteristics 500 come about by the superimposition, shown in FIG. 5, of first layer 102 and second layer 103 about infrared source 10. The superimposition in FIG. 8 of bandpass filter characteristics 500 by filter transmission curve 600 of interference filter 32 shows that the operating frequency range, that is indicated in FIG. 8 by reference numeral 501 and a double arrow includes only a single pass frequency of interference filter 32. This pass frequency corresponds to eleventh wavelength 61, about which first filter transmission sub-curve 610 is situated. The additional or adjacent filter transmission sub-curves 620, 640, which are located at twelfth and fourteenth wavelengths 62, 64, lie outside operating frequency range 501.

What is claimed is:

1. An infrared source for a gas sensor comprising:
    a coated lamp glass including;
        a first layer having first transmission characteristics produced by absorption of infrared radiation; and
        a second layer having second transmission characteristics produced by absorption of infrared radiation,
        wherein a combination of the first and the second transmission characteristics effects a bandpass filter characteristics for an operating frequency range, and wherein the first and second transmission characteristics are different transmission characteristics.

2. The infrared source according to claim 1, wherein the first transmission characteristics with respect to the operating frequency range provides a higher transmission for shorter wavelengths, and the second transmission characteristics with respect to the operating frequency range provides a higher transmission for longer wavelengths.

3. The infrared source according to claim 1, wherein the first layer includes glass, and the second layer includes one of silicon and germanium.

4. A gas sensor comprising:
    an infrared source;
    a detector; and
    an interference filter situated between the infrared source and the detector, wherein the infrared source includes:
    a coated lamp glass including;
        a first layer having first transmission characteristics produced by absorption of infrared radiation, and
        a second layer having second transmission characteristics produced by absorption of infrared radiation,
        wherein a combination of the first and the second transmission characteristics effects a bandpass filter characteristics for an operating frequency range, and wherein the first and second transmission characteristics are different transmission characteristics.

5. The gas sensor according to claim 4, wherein the operating frequency range of the infrared source includes exactly one pass frequency of the interference filter.

6. The gas sensor according to claim 4, wherein the interference filter is a Fabry-Perot filter.

7. The infrared source of claim 1, wherein the first layer and second layer are both positioned along a same line of transmission of infrared radiation from the infrared source.

8. The infrared source of claim 7, wherein the infrared source is configured so that infrared radiation from the infrared source travels along the line of transmission through the first layer before traveling through the second layer.

9. The infrared source of claim 1, wherein the first layer has a top surface directly contacting a bottom surface of the second layer.

10. The gas sensor of claim 4, wherein the first layer and second layer are both positioned along a same line of transmission of infrared radiation from the infrared source.

11. The gas sensor of claim 10, wherein the infrared source is configured so that infrared radiation from the infrared source travels along the line of transmission through the first layer before traveling through the second layer.

12. The gas sensor of claim 4, wherein the first layer has a top surface directly contacting a bottom surface of the second layer.

13. The gas sensor of claim 4, wherein the operating frequency range of the infrared source includes exactly one pass frequency of the interference filter, wherein the first layer and second layer are both positioned along a same line of transmission of infrared radiation from the infrared source, wherein the infrared source is configured so that infrared radiation from the infrared source travels along the line of transmission through the first layer before traveling through the second layer, wherein the interference filter is a Fabry-Perot filter, and wherein the first layer has a top surface directly contacting a bottom surface of the second layer.

14. The gas sensor of claim 13, wherein the first transmission characteristics with respect to the operating frequency range provides a higher transmission for shorter wavelengths, and the second transmission characteristics with respect to the operating frequency range provides a higher transmission for longer wavelengths, and wherein the first layer includes glass, and the second layer includes one of silicon and germanium.

15. The gas sensor of claim 4, wherein the first transmission characteristics with respect to the operating frequency range provides a higher transmission for shorter wavelengths, and the second transmission characteristics with respect to the operating frequency range provides a higher transmission for longer wavelengths, and wherein the first layer includes glass, and the second layer includes one of silicon and germanium.

16. The infrared source of claim 1, wherein the operating frequency range of the infrared source includes exactly one pass frequency of the interference filter, wherein the first layer and second layer are both positioned along a same line of transmission of infrared radiation from the infrared source, wherein the infrared source is configured so that infrared radiation from the infrared source travels along the line of transmission through the first layer before traveling through the second layer, wherein the interference filter is a Fabry-Perot filter, and wherein the first layer has a top surface directly contacting a bottom surface of the second layer.

17. The infrared source of claim 16, wherein the first transmission characteristics with respect to the operating frequency range provides a higher transmission for shorter wavelengths, and the second transmission characteristics with respect to the operating frequency range provides a higher transmission for longer wavelengths, and wherein the first layer includes glass, and the second layer includes one of silicon and germanium.

18. The infrared source of claim 1, wherein the first transmission characteristics with respect to the operating frequency range provides a higher transmission for shorter wavelengths, and the second transmission characteristics with respect to the operating frequency range provides a higher transmission for longer wavelengths, and wherein the first layer includes glass, and the second layer includes one of silicon and germanium.

* * * * *